United States Patent [19]

Riethmann et al.

[11] 4,191,621
[45] Mar. 4, 1980

[54] PROCESS FOR THE PRODUCTION OF SUBSTITUTED BENZAL AND BENZYL BROMIDES

[75] Inventors: Jean Riethmann, Rheinfelden; Franz Marti, Dornach; Tibor Somlo, Birsfelden, all of Switzerland

[73] Assignee: Ciba-Geigy Aktiengesellschaft, Basel, Switzerland

[21] Appl. No.: 945,957

[22] Filed: Sep. 26, 1978

[30] Foreign Application Priority Data

Sep. 30, 1977 [CH] Switzerland .................. 11985/77

[51] Int. Cl.$^2$ .............................................. B01J 1/10
[52] U.S. Cl. ........................ 204/158 HA; 204/163 R
[58] Field of Search ................. 204/158 HA, 163 R

[56] References Cited

U.S. PATENT DOCUMENTS 3,190,825  6/1965  Huyser ..................... 204/158 HA

*Primary Examiner*—Howard S. Williams
*Attorney, Agent, or Firm*—Sprung, Felfe, Horn, Lynch & Kramer

[57] ABSTRACT

The invention describes a process for the production of benzal or benzyl bromides which contain electrophilic substituents in the ortho- and/or para-position, or mixtures thereof, by the side-chain bromination of correspondingly substituted toluene, which comprises introducing elementary chlorine, under irradiation with visible light, into a two-phase system consisting of an aqueous phase and an organic phase and containing a correspondingly substituted toluene, at least one metal bromide, and a base, and also the compounds obtained by this process.

13 Claims, No Drawings

PROCESS FOR THE PRODUCTION OF SUBSTITUTED BENZAL AND BENZYL BROMIDES

It is known that it is exceedingly difficult to obtain benzal and benzyl bromides which contain an electrophilic substituent in the ortho- and/or para-position.

The side-chain brominations of correspondingly substituted alkyl benzenes with elementary bromine require in some cases high temperatures. According to Houben-Weyl, Vol. 5/4, 5334–337, nitrotoluenes for example are brominated in a bomb tube or in a pressure flask at 100° to 160° C. In view of the low thermal stability of many aralkyl bromides, for example o-nitrobenzyl bromide or o-nitrobenzal bromide, these known methods often give rise to difficulties.

Even the side-chain brominations of o-nitrotoluene in a carbon tetrachloride/water mixture using elementary bromine and under UV-irradiation, which have been described recently in German Democratic Republic patent specifications Nos. 74279 and 82463, provide only o-nitrobenzyl bromide in a yield of 45 to 55%. The process described in German Democratic Republic patent specification 118609 affords a somewhat better yield when o-nitrotoluene is brominated in carbon tetrachloride under irradiation with visible or ultra-violet light or using peroxide as catalyst; but in this process too it was not possible to obtain either o-nitrobenzal bromide or a complete sidechain bromination of o-nitrotoluene to yield o-nitrobenzyl bromide.

It has now been found that substituted benzal or benzyl bromides or mixtures thereof, of the general formulae

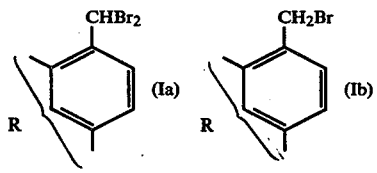

wherein R represents an electrophilic substituent in the ortho- and/or para-position, can be obtained in excellent yield and purity while avoiding the aforementioned disadvantages.

The novel process comprises introducing elementary chlorine, under irradiation with visible light, into a two-phase system consisting of an aqueous phase and an organic phase and containing a correspondingly substituted toluene, at least one metal bromide, and a base.

Examples of electrophilic substituents R are the nitro group, the cyano group or a halogen atom, for example chlorine, bromine, iodine or fluorine.

Suitable metal bromides are in particular alkali metal bromides or alkaline earth metal bromides, such as magnesium bromide, especially potassium or calcium bromide and preferably sodium bromide.

As bases it is possible to use metallic bases, for example alkali metal bases or alkaline earth metal bases which contain a hydroxyl, hydrogen carbonate or carbonate ion, or anion exchangers in hydroxyl ion form, for example Dowex 2 ® (quaternary ammonium hydroxides).

In particular, it is possible to use sodium or potassium hydroxide, sodium or potassium hydrogen carbonate or sodium or potassium carbonate. In analogous manner, the corresponding hydroxides, hydrogen carbonates and carbonates of calcium and magnesium can be used as bases.

The pH of the reaction mixture is determined by the nature and amount of the base employed and is in the range from 3 to 11, preferably 4 to 9. A preferred embodiment is to establish an initial pH value between 6 and 8, for example with a buffer salt, such as an alkali salt of phosphoric acid, acetic acid, propionic acid or benzoic acid, and to maintain this pH value during the reaction by addition of one of the bases referred to above.

The reaction is carried out in a pH range from 4 to 11, preferably 4 to 9, when using a readily water-soluble base, for example an alkali base. If the reaction is carried out in the presence of a base which is sparingly soluble in water, for example an alkaline earth carbonate, such as calcium carbonate, then the pH value falls below 7.5 to about 4.

The metallic base is used as neutralising agent. This is present in the aqueous phase. The hydrogen chloride which forms during the reaction is extracted from the organic phase by thorough mixing of both phases (vigorous stirring, flow mixing) and immediately neutralised.

The reaction is preferably carried out in the temperature range between 0° and 120° C., but preferably at a temperature between 30° and 90° C.

The educt, the substituted toluene itself, can be employed as organic phase. However, it is advantageous to employ inert and as far as possible apolar solvents, in particular halogenated aromatic hydrocarbons, for example chlorobenzenes or bromobenzenes, and also nitrobenzene, as well as carbon disulfide or halogenated alkanes, preferably carbon tetrachloride, methylene chloride, chloroform, tetrachloroethane or hexachloroethane.

It is expedient to stir the reaction mixture continuously in order to achieve a thorough mixing of the two-phase system.

The side-chain bromination is carried out under irradiation with visible light, i.e. in the range from 3800 to 8000 Å. Suitable sources of light for the process of the invention are tungsten lamps, for example incandescent filaments or fluorescent tubes, discharge lamps, doped mercury lamps, sodium vapour lamps, xenon lamps etc. Sodium vapour lamps and tungsten lamps are preferred.

The reaction vessels are irradiated externally with the light sources, or immersion lamps for visible light, which can be built into metallic reaction vessels, are employed. In order to prevent losses of light in glass reaction vessels, it is advantageous to provide these latter with a layer which reflects light (metal casing, jacket of aluminium foil).

The advantages of the side-chain bromination of ortho-substituted toluenes in accordance with the present invention are that, compared with the prior art, it is now possible to prepare a mixture of benzyl and benzal bromide which contains no starting material, or else also pure benzyl or benzal bromide, without the formation of corresponding benzotribromides. Moreover, yields of benzyl and/or benzal bromide, based on the amount of reacted toluenes, of about 90 to 100% of theory are obtained. The bromination is carried out without the use of elementary bromine, for example in accordance with the following reaction schemes:

$$R\text{—}CH_3 + 2NaBr + 2NaOH + 2Cl_2 \rightarrow R\text{—}CHBr_2 + 4NaCl + 2H_2O,$$

i.e. only about 2 moles of sodium bromide are required to obtain benzal bromide, as the bromination proceeds virtually uniformly; or $$R\text{—}CH_3 + NaBr + NaOH + Cl_2 \rightarrow R\text{—}CH_2Br + 2NaCl + H_2O.$$

The difficulties involved in the use of elementary bromine (transportation, addition, regeneration and the toxicological and corrosion problems connected therewith) consequently do not arise.

The presence of the base prevents the escape of hydrogen chloride and hydrogen bromide. There are also no wastewater problems. The wastewater consists solely of aqueous sodium chloride solution.

During the further processing of the benzyl and/or benzal bromides, for example in the course of the reaction $$R\text{—}CHBr_2 + 2NaOH \rightarrow R\text{—}CHO + 2NaBr + H_2O$$

aqueous sodium bromide is formed, which can be re-used direct for the bromination in the present process. The expensive recovery of the bromine from the resulting bromide salts is thus dispensed with.

The chlorobromine product, R—CHClBr, can result as virtually the only by-product. It is also saponified without difficulty to the same aldehyde as the corresponding benzal bromide.

The o-nitrobenzyl bromide obtained by the process of the present invention is an important intermediate for the production of o-nitrobenzyl alcohol, o-nitrobenzaldehyde and bromohexine [N-cyclohexyl-N-methyl-N-(2-amino-3,5-dibromobenzyl)-ammonium chloride].

The benzal bromides obtained by the process of the present invention can be used as intermediates for the production of the corresponding benzaldehydes. In addition, the mixture of o-substituted benzyl and benzal bromides can be converted, according to the invention, into a mixture consisting of the formate of the corresponding benzyl alcohol and the corresponding benzaldehyde by addition of an alkali formiate. This mixture can be converted by hydrolysis and subsequent oxidation with aqueous nitric acid to give the corresponding benzaldehyde.

The o-nitrobenzaldehyde which can be obtained from o-nitrobenzal bromide, or from the mixture of o-nitrobenzyl or o-nitrobenzal bromide, is a valuable intermediate and can be used, for example, for the indigo synthesis of A. v. Baeyer. o-Nitrobenzaldehyde is also used as a diagnostic agent in medicine, for example in diabetes.

o-Cyanobenzyl bromide and/or o-cyanobenzal bromide can be used for the preparation of o-cyanobenzaldehyde. o-Cyanobenzaldehyde is used as an intermediate for the preparation of anti-hypertensive pharmaceutical preparations with coronary dilating and peripherally dilating action (cf. German Offenlegungsschrift No. 1,963,188) and as starting product for the preparation of o-cyanocinnamic acids which are important for pharmaceutical syntheses. In addition, o-cyanobenzaldehyde is used as a stabilising additive for methyl chloroform (cf. U.S. Pat. No. 3,364,270) and as additive for fibres containing polyvinyl alcohol to improve their elasticity and dyeability (cf. U.S. Pat. No. 3,071,429).

The invention is illustrated by the following Examples, in which the parts are by weight.

EXAMPLE 1

137 g (1 mole) of o-nitrotoluene are dissolved in 1590 g (1000 ml) of carbon tetrachloride. Then 253 g (2.46 moles) of sodium bromide and 120 g (1.2 moles) of calcium carbonate in 600 g of water are added and the mixture is heated to reflux temperature with stirring. While externally irradiating the glass flask with three 150 watt sodium high-pressure lamps, 170 g (2.39 moles) of chlorine gas are introduced such that the bromine set free is always just consumed. After cooling, the phases are separated. The aqueous phase is extracted with carbon tetrachloride and the combined organic phases are dried over sodium sulfate and concentrated, affording 285 g of a mixture consisting of 96.4 parts of o-nitrobenzal bromide (93.1% of theory) and 3.6 parts of o-nitrobenzyl bromide (4.7% of theory).

EXAMPLE 2

274 g (2 moles) of o-nitrotoluene are dissolved in 3180 g (2000 ml) of carbon tetrachloride and 433 g of sodium bromide in the form of a 25% solution are added. In a circulating apparatus with a centrally positioned 150 watt sodium high-pressure lamp, 424 g of chlorine are introduced at reflux temperature and under irradiation such that the bromine which forms is always just consumed. Simultaneously the pH value is kept at 7.5 with 30% sodium hydroxide solution (consumption 314 g). After 14 hours, working up is effected as described in Example 1, affording 575 g of a mixture consisting of 92.5 parts of o-nitrobenzal bromide (90.8% of theory), 3.4 parts of o-nitrobenzyl bromide (4.6% of theory), and 4 parts of ω-bromo-ω-chloro-2-nitrotoluene (4.7% of theory).

EXAMPLE 3

137 g of o-nitrotoluene are reacted with 103 g of sodium bromide, 85 g of calcium carbonate and 127 g of chlorine for 4 hours as described in Example 1. Working up yields 255 g of a mixture consisting of 39.7 parts of o-nitrobenzyl bromide (47% of theory), 54 parts of o-nitrobenzal bromide (46.8% of theory) and 6 parts of ω-bromo-ω-chloro-2-nitrotoluene (6.2% of theory).

EXAMPLE 4

A forced circulation apparatus is charged with a solution of 274 g (2 moles) of o-nitrotoluene in 3000 g (about 2 liters) of carbon tetrachloride and also with an aqueous solution containing 500 ml of water, 453 g (4.4 moles) of sodium bromide and 10 g of disodium hydrogen phosphate (0.08 mole). The mixture is circulated around a 150 watt sodium high-pressure lamp and heated to reflux. Under reflux and irradiation, 340 g (4.8 moles) of chlorine gas are introduced and simultaneously the pH value is kept constantly at 6 to 6.5 by the dropwise addition of aqueous sodium hydroxide solution. The chlorine gas must be introduced at such a rate that the bromine set free is always just consumed. In the course of about 6 hours the addition of chlorine is complete and virtually the entire amount has been reacted to o-nitrotoluene. After cooling, the phases are separated and the carbon tetrachloride phase is concentrated, affording 570 g of o-nitrobenzal bromide (content 99%).

EXAMPLE 5

A forced circulation apparatus is charged with 685 g (5 moles) of o-nitrotoluene and an aqueous solution containing 1250 ml of water, 280 g (2.7 moles) of sodium bromide and 25 g (0.2 mole) of disodium hydrogen phosphate. The mixture is circulated around a 150 watt sodium high-pressure lamp and, at reflux and under irradiation, 210 g (2.96 moles) of chlorine gas are added while also adding sufficient sodium hydroxide solution to maintain a constant pH value of 6 to 6.5. When all the sodium bromide has been consumed, the mixture is cooled and the organic phase is separated and dried over sodium sulfate. On cooling the mixture to $-10°$ C., o-nitrobenzyl bromide crystallises out. Yield: 540 g after filtration and drying. The mother liquor, which contains o-nitrotoluene, o-nitrobenzyl bromide and a small amount of o-nitrobenzal bromide, can be re-used in a fresh reaction.

EXAMPLE 6

A solution of 234 g (2 moles) of o-cyanotoluene in 3000 g (2 liters) of carbon tetrachloride and a solution of 500 ml of water, 453 g of sodium bromide and 10 g of disodium hydrogen phosphate are reacted with 340 g of chlorine gas and with the necessary amount of sodium hydroxide solution to maintain a pH value of 6 to 6.5, as described in Example 4. Yield: 522 g of o-cyanobenzal bromide (content about 99%).

What is claimed is:

1. A process for the production of benzal or benzyl bromides which contain electrophilic substituents in the ortho- and/or para-position, or mixtures thereof, by the side-chain bromination of correspondingly substituted toluene, which comprises introducing elementary chlorine, under irradiation with visible light, into a two-phase system consisting of an aqueous phase and an organic phase and containing a correspondingly substituted toluene, at least one metal bromide, and a base.

2. A process according to claim 1, which comprises the use of a metallic base.

3. A process according to claim 1, which comprises the use of an alkali metal base or an alkaline earth metal base.

4. A process according to claim 1, which comprises the use of a water-soluble alkali metal hydroxide or alkaline earth metal hydroxide.

5. A process according to claim 1, which comprises the use of an alkali metal carbonate or alkaline earth metal carbonate.

6. A process according to claim 1, which comprises the use of sodium carbonate or calcium carbonate.

7. A process according to claim 1, wherein the bromination is carried out at a temperature between 0° and 120° C.

8. A process according to claim 7, wherein the bromination is carried out at a temperature between 30° and 90° C.

9. A process according to claim 1, wherein a tungsten lamp or sodium vapour lamp is used as source of visible light.

10. A process according to claim 1, wherein an alkali metal bromide or alkaline earth metal bromide is used as metal bromide.

11. A process according to claim 10, wherein sodium bromide, potassium or calcium bromide is used as metal bromide.

12. A process according to claim 10 wherein sodium bromide is used as metal bromide.

13. A process according to claim 1, wherein the reaction is carried out in the presence of a buffer salt at a pH value of 6 to 8.

* * * * *